United States Patent
Lee et al.

(10) Patent No.: US 10,264,973 B2
(45) Date of Patent: Apr. 23, 2019

(54) OPTICAL COHERENCE TOMOGRAPHY DEVICE

(71) Applicant: LG ELECTRONICS INC., Seoul (KR)

(72) Inventors: Jun Lee, Seoul (KR); Jungho Chung, Seoul (KR); Hoseong Song, Seoul (KR); Yujin Oh, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/712,843

(22) Filed: Sep. 22, 2017

(65) Prior Publication Data

US 2018/0078141 A1    Mar. 22, 2018

Related U.S. Application Data

(60) Provisional application No. 62/398,496, filed on Sep. 22, 2016.

(30) Foreign Application Priority Data

Nov. 15, 2016    (KR) .................. 10-2016-0152104

(51) Int. Cl.
*G01J 3/45* (2006.01)
*A61B 5/00* (2006.01)
(Continued)

(52) U.S. Cl.
CPC ............ *A61B 5/0066* (2013.01); *A61B 5/441* (2013.01); *G02B 21/0052* (2013.01);
(Continued)

(58) Field of Classification Search
CPC .. A61B 5/0066; A61B 5/441; G02B 21/0052; G01B 9/02002; G01B 9/02044;
(Continued)

(56) References Cited

U.S. PATENT DOCUMENTS

2007/0150128 A1\* 6/2007 Fowell .................. B64G 1/361
  701/13
2007/0183643 A1\* 8/2007 Jayaraman ............. A61B 3/102
  382/131

(Continued)

FOREIGN PATENT DOCUMENTS

KR    1020150043115    4/2015
KR    1020150136632    12/2015

OTHER PUBLICATIONS

PCT International Application No. PCT/KR2017/010417, International Search Report dated Jan. 29, 2018, 3 pages.

*Primary Examiner* — Tarifur R Chowdhury
*Assistant Examiner* — Jonathon Cook
(74) *Attorney, Agent, or Firm* — Lee, Hong, Degerman, Kang & Waimey

(57) ABSTRACT

According to one embodiment, an Optical Coherence Tomography (OCT) device includes: a light source; a mirror to reflect a light from the light source; a light receiver to output the light from the light source to skin and receive a light reflected from the skin; a detector to detect an interference signal between the light reflected from the mirror and the light received by the light receiver; an image sensor to convert the detected interference signal into an image signal; a processor to output a second signal by filtering a first signal based on the image signal, calculate an error by using the first signal and the second signal, and output an error-compensated image by compensating for the calculated error; and a display to display the error-compensated image. In this configuration, the OCT device may reduce noise caused by the image sensor, to display a skin image with improved quality.

17 Claims, 17 Drawing Sheets

(51) Int. Cl.
  *G02B 21/00* (2006.01)
  *A61B 17/00* (2006.01)
(52) U.S. Cl.
  CPC ........... *A61B 5/7203* (2013.01); *A61B 5/7257* (2013.01); *A61B 2017/00057* (2013.01)
(58) Field of Classification Search
  CPC ........... G01B 9/02062; G01B 9/02083; G01B 9/02091; G05B 2219/41151
  USPC ........................................................ 356/497
  See application file for complete search history.

(56) References Cited

U.S. PATENT DOCUMENTS

| | | | |
|---|---|---|---|
| 2008/0100612 A1* | 5/2008 | Dastmalchi | A61B 3/102 345/418 |
| 2010/0098337 A1* | 4/2010 | Tsukamoto | G09G 3/2018 382/190 |
| 2012/0138586 A1* | 6/2012 | Webster | A61B 18/20 219/121.64 |
| 2012/0188538 A1* | 7/2012 | Patil | A61B 3/102 356/301 |
| 2013/0044313 A1* | 2/2013 | Rolland | G01J 3/02 356/51 |
| 2013/0135614 A1* | 5/2013 | Wax | G01N 21/49 356/300 |
| 2014/0085454 A1* | 3/2014 | Lim | H04N 5/21 348/80 |
| 2014/0218363 A1* | 8/2014 | Dastmalchi | A61B 3/102 345/424 |
| 2014/0313477 A1 | 10/2014 | Raymond et al. | |
| 2015/0043003 A1 | 2/2015 | Chung et al. | |
| 2017/0024910 A1* | 1/2017 | Griffin | G06T 11/003 |

* cited by examiner

OPTICAL COHERENCE TOMOGRAPHY DEVICE

CROSS-REFERENCE TO RELATED APPLICATION

Pursuant to 35 U.S.C. § 119, this application claims the benefit of U.S. Provisional Application No. 62/398,496, filed on Sep. 22, 2016, and also claims the right of priority to Korean Application No. 10-2016-0152104, filed on Nov. 15, 2016, the contents of which are all incorporated by reference herein in their entirety.

BACKGROUND OF THE INVENTION

1. Field of the invention

The present invention relates to an Optical Coherence Tomography (OCT) device, and more particularly, to an OCT device which reduces noise caused by an image sensor, thereby enabled to display a skin image with improved quality.

2. Description of the Related Art

As medical devices for displaying an image of skin or internal body, a number of devices are being used, including an X-ray system, a Computerized Tomography (CT) scanner, a Magnetic Resonance Image (MRI) device, and an ultrasound system.

Meanwhile, as a device for displaying a skin image, an Optical Coherence Tomography (OCT) device can be used.

The OCT device is a tomography device which noninvasively captures a cross-sectional view of a sample at micrometer resolution based on interference properties of light.

Such an OCT device is used in many fields such as ophthalmology, cardiology, and dermatology for clinical purposes.

In addition, efforts are being made to study a technology that enables the OCT device to display a clear skin image without noise.

SUMMARY OF THE INVENTION

The present invention has been made in view of the above problems, and it is one object of the present invention to provide an Optical Coherence Tomography (OCT) device which reduces noise caused by an image sensor, thereby enabled to display a skin image with improve quality.

In accordance with an embodiment of the present invention, the above and other objects can be accomplished by the provision of an Optical Coherence Tomography (OCT) device including: a light source; a mirror to reflect a light from the light source; an light receiver to output the light from the light source to skin and receive a light reflected from the skin; a detector to detect an interference signal between the light reflected from the mirror and the light received by the light receiver; an image sensor to convert the interference signal, detected by the detector, into an image signal; a processor to output a second signal by filtering a first signal being based on the image signal from the image sensor, calculate an error by using the first signal and the second signal, and output an error-compensated image by compensating for the calculated error; and a display to display the error-compensated image.

In accordance with another embodiment of the present invention, the above and other objects can be accomplished by the provision of an Optical Coherence Tomography (OCT) device including: a probe to output a light to skin and receive a light reflected from the skin; a spectrometer to detect an interference signal between a light reflected from a mirror and the light received by the probe; an image sensor to convert the interference signal, detected by the spectrometer, into an image signal; a processor to calculate an error, caused by a difference in pixels of the image sensor, in the image signal from the image sensor, and output an error-compensated image by compensating for the calculated error; and a display to display the error-compensated image.

The details of other embodiments are included in the following description and the accompanying drawings.

BRIEF DESCRIPTION OF THE DRAWINGS

The embodiments will be described in detail with reference to the following drawings in which like reference numerals refer to like elements wherein.

DETAILED DESCRIPTION OF THE PREFERRED EMBODIMENTS

Hereinafter, the embodiments disclosed in the present specification will be described in detail with reference to the accompanying drawings.

In the following description, with respect to constituent elements used in the following description, the suffixes "module" and "unit" are used or combined with each other only in consideration of ease in the preparation of the specification, and do not have or serve as different meanings. Accordingly, the suffixes "module" and "unit" may be interchanged with each other.

An Optical Coherence Tomography (OCT) device described throughout this specification is an OCT device which is able to be attached to a cylindrical case and to provide medication guides.

Figure 1:
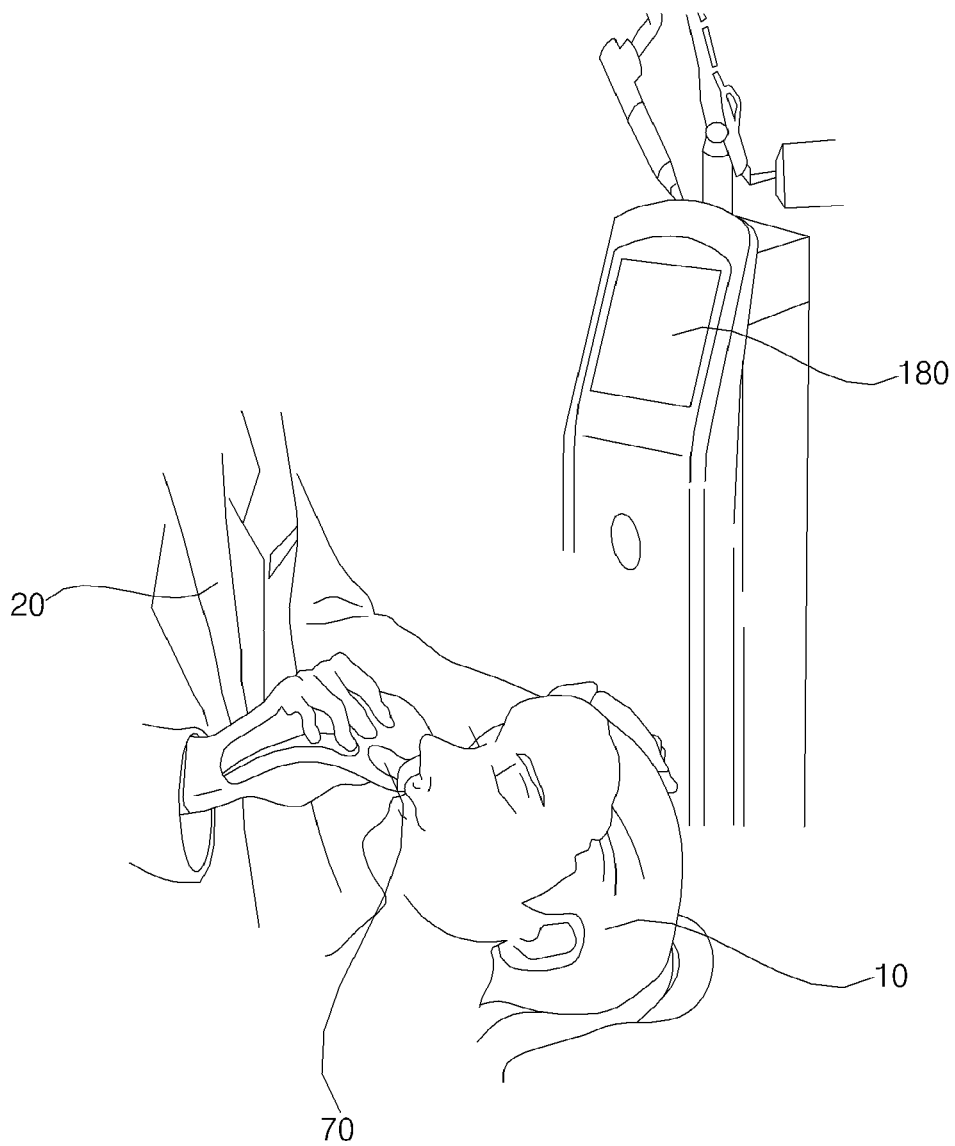
FIG. 1 is a diagram illustrating an Optical Coherence Tomography (OCT) device according to an embodiment of the present invention.

FIG. 1 is a diagram illustrating an OCT device according to an embodiment of the present invention.

Referring to the drawing, an OCT device 100 according to an embodiment of the present invention is a device for displaying a skin image, which is a tomography device that non-invasively captures a cross-sectional view of a sample at micrometer resolution by using interference properties of light.

As shown in the drawing, when a user 20 puts a probe 70 of the OCT device 100 in contact with the skin of a patient 10, an image corresponding to depth of the skin is displayed on a display 180.

The OCT device 100 may include an image sensor 160 (see FIG. 2), and use the image sensor 160 (see FIG. 2) to convert an interference signal between a light output to the skin and a light received from the skin into an image signal.

Meanwhile, the image sensor 160 (see FIG. 2) includes a plurality of pixels to convert a light interference signal into an image signal, and a difference in the pixels may cause noise. Due to the noise, an image corresponding to depth of the skin may be displayed unclearly.

The present invention provides the OCT device 100 which reduces noise caused by an image sensor, thereby enabled to display a skin image with improved quality.

Accordingly, the OCT device 100 includes: a light source 110; a mirror 135 to reflect a light from the light source 110; a light receiver 130 to output a light from the light source 110 to the skin and receive a light reflected from the skin; a detector 150 to detect an interference signal between the light reflected by the mirror 135 and the light received by the light receiver 130; an image sensor 160 to convert the interference signal, detected by the detector 150, into an image signal; a processor 170 to output a second signal by filtering a first signal being based on the image signal from the image sensor 160, calculate an error by using the first signal and the second signal, and output an error-compensated image by compensating for the calculated error; and a display 180 to display the error-compensated image. In this configuration, the OCT device 100 reduces noise caused by the image sensor 160, thereby enabled to display a skin image with improved quality. In particular, it is possible to display an image in which an error has been compensated with respect to depth of the skin.

In particular, during a first frame interval, the processor 170 outputs a second signal by filtering a first signal being based on an image signal from the image sensor 160, and calculates an error by using the first signal and the second signal. Then, during a second frame interval, the processor 170 outputs an error-compensated image by compensating for the calculated error. In this manner, it is possible to perform error compensation in real time and therefore display a skin image with improved quality.

Meanwhile, when image signals are received from the image sensor 160, the processor 170 may continuously perform error compensation. In this manner, it is possible to perform error compensation in real time and therefore display a skin image with improved quality.

Meanwhile, an OCT device 100 according to another embodiment of the present invention includes: a probe 70 to output a light to the skin and receive a light reflected from the skin; a spectrometer 155 to detect an interference signal between a light reflected by a mirror 135 and a light received by a light receiver 130; an image sensor 160 to convert the interference signal, detected by the spectrometer 155, into an image signal; a processor 170 to calculate an error, caused by a difference in pixels of the image sensor, in the image signal from the image sensor, and output an error-compensated image by compensating for the calculated error; and a display 180 to display the error-compensated image. Due to this configuration, the OCT device 100 reduces noise caused by the image sensor, thereby enabled to display a skin image with improved quality.

Operations of the OCT device 100 according to the present invention are described in more detail with reference to FIG. 2.

Figure 2:
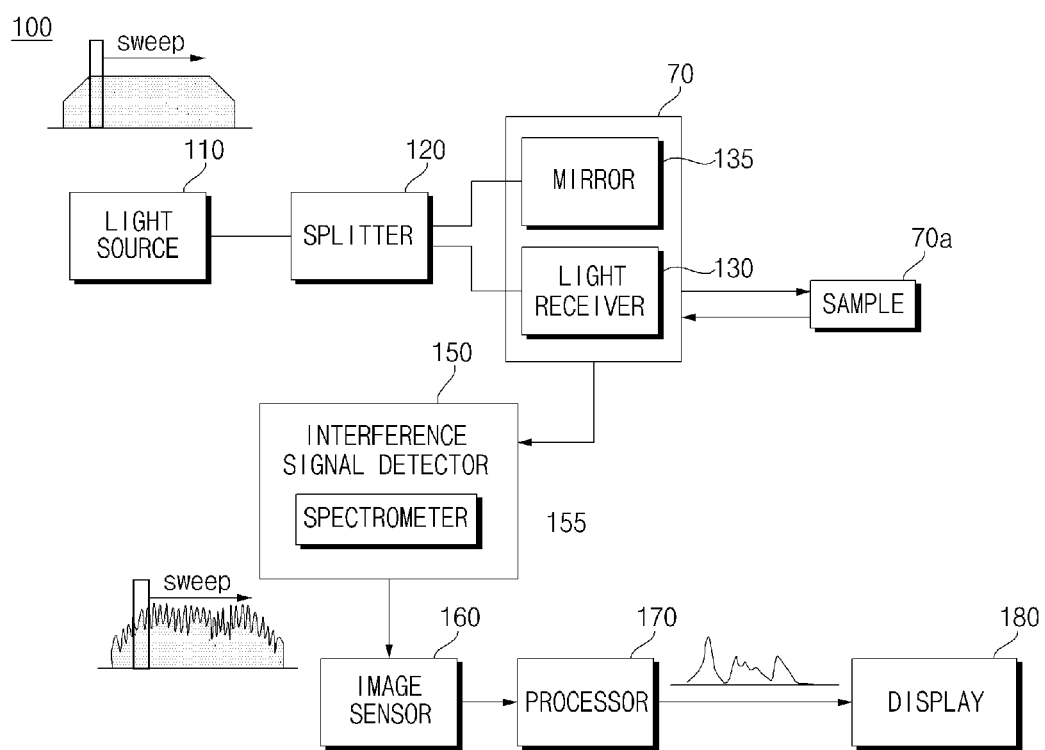
FIG. 2 is an internal block diagram illustrating an example of the OCT device shown in FIG. 1.

FIG. 2 is a block diagram of an example of the OCT device shown in FIG. 1.

Referring to the drawing, the OCT device 100 may include a light source 110, a splitter 120, a probe 70, an interference signal detector 150, an image sensor 160, a processor 170, and a display 180.

The light source 110 outputs a light. In order to output a light to a sample 70$a$, such as skin, the light source 110 may output an infrared light, a visible light, or an ultraviolet light. In the following, the light source 110 is described as outputting a visible light.

In the drawing, an exemplary case in which the light source 110 outputs light with a predetermined bandwidth in a sweeping manner.

The splitter 120 splits a path of light output from the light source 110. Specifically, the splitter 120 directs the light, output from the light source 110, to a mirror 135 within the probe 70 and to the light receiver 130.

Meanwhile, the splitter 120 may include a beam splitter or a directional coupler.

The mirror 135 within the probe 170 may be referred to as a reference surface, which is disposed to compare with a light reflected from the sample.

Meanwhile, the mirror 135 may be disposed outside the probe 70.

Meanwhile, the mirror 135 reflects light output from the light source 110. The light reflected by the mirror 135 is delivered to the interference signal detector 150.

Meanwhile, the probe 70, especially, the light receiver 130, outputs a light to the sample 70$a$ which is the skin of a patient. Then, the probe 70 receives a light reflected from the sample 70$a$ which is the skin. Meanwhile, the light receiver 130 may be referred to as a system for measuring a sample.

The light reflected from the skin is delivered from the probe 70, particularly, the light receiver 130, to the interference signal detector 150.

The interference signal detector 150 may detect an interference signal between a light reflected from the mirror 135 and a light received by the light receiver 130.

To this end, the interference signal detector 150 may include a spectrometer 155 that decomposes an interference signal, which is between a light reflected from the mirror 135 and a light received by the light receiver 130, into different wavelengths.

Meanwhile, unlike the embodiment shown in the drawing, the spectrometer 155 may be disposed before the interference signal detector 150. In this case, the spectrometer 155 may decompose an interference signal between a light reflected from the mirror 135 and a light received by the light receiver 130, into different wavelengths, and then the interference signal detector 150 may detect the interference signal.

Alternatively, unlike the embodiment shown in the drawing, it is possible to use only the spectrometer 155 without the interference signal detector 150.

The image sensor 160 may convert an interference signal from the interference signal detector 150 into an image signal.

The image sensor 160 may include a plurality of pixels, and output an image signal by detecting an interference signal, which is decomposed into wavelengths by the interference signal detector 150, at each pixel.

The processor 170 may compensate for an error caused by the image sensor 160, and output an error-compensated image.

The display 180 may display the error-compensated image. In particular, the display 180 may display an error compensated image corresponding to depth of the skin. Accordingly, a skin image with improved quality may be displayed by reducing noise caused by the image sensor 160. In particular, it is possible to display an image in which an error has been compensated with respect to depth of the skin by reducing noise caused by the image sensor 160.

Meanwhile, the processor 170 may output a second signal by filtering a first signal being based on the image signal from the image sensor 160, calculate an error by using the first signal and the second signal, and output an error-compensated image by compensating for the calculated error.

In particular, during a first frame interval, the processor 170 may output a second signal by filtering a first signal being based on an image signal from the image sensor 160, and calculate an error by using the first signal and the second signal. Then, during a second frame interval, the processor 170 may output an error-compensated image by compensating for the calculated error. In this manner, it is possible to perform error compensation in real time and therefore display a skin image with improved quality.

Meanwhile, the processor 170 may calculate the error based on a ratio between the first signal and the second signal, compensates an image signal from the image sensor 160 by using an inverse of the calculated error, and output an error-calculated image.

Meanwhile, the processor 170 may perform error compensation on each horizontal or vertical line of an image signal from the image sensor 160.

Meanwhile, when image signals are received from the image sensor 160, the processor 170 may continuously perform error compensation. In this manner, it is possible to perform error compensation in real time and therefore display a skin image with improved quality.

Meanwhile, the processor 170 includes a filter 570 for outputting a second signal by filtering a first signal, and the filter 570 may output the second signal based on a moving average of the first signal.

Meanwhile, the processor 170 may include: an interpolator 510 for interpolating an image signal from the image sensor 160; an error compensator 515 for compensating the interpolated image signal by using a calculated error; a converter 530 for converting the error-compensated image signal into frequency domain; and a background subtractor 540 for removing the background from the image signal from the converter 530 and outputting an error-compensated image from which the background has been removed.

Meanwhile, the processor 170 may further include: an inverse-converter 560 which converts an image signal from the background subtractor 540 into time domain; a filter 570 which outputs a second signal by filtering a first signal from the inverse-converter 560; and an error calculator 580 which calculates an error by using the first signal and the second signal.

Meanwhile, the processor 170 may further include a second filter 520 which is disposed (e.g., coupled) between the error compensator 515 and the converter 530 and to filter an error, caused by the mirror 135, from the error-compensated image signal.

Meanwhile, during a first frame interval, the processor 170 may output a second signal by filtering a first signal being based on an image signal from the image sensor 160 by means of the inverse-converter 560 and the error calculator 580, and calculate an error using the first signal and the second signal. Then, during a second frame interval, the processor 170 may output an error-compensated image by compensating for the calculated error by means of the error calculator 580, the converter 530, and the background subtractor 540.

FIGS. 3A to 4D are diagrams referenced to explain operation of the OCT device shown in FIG. 1.

Figure 3A:
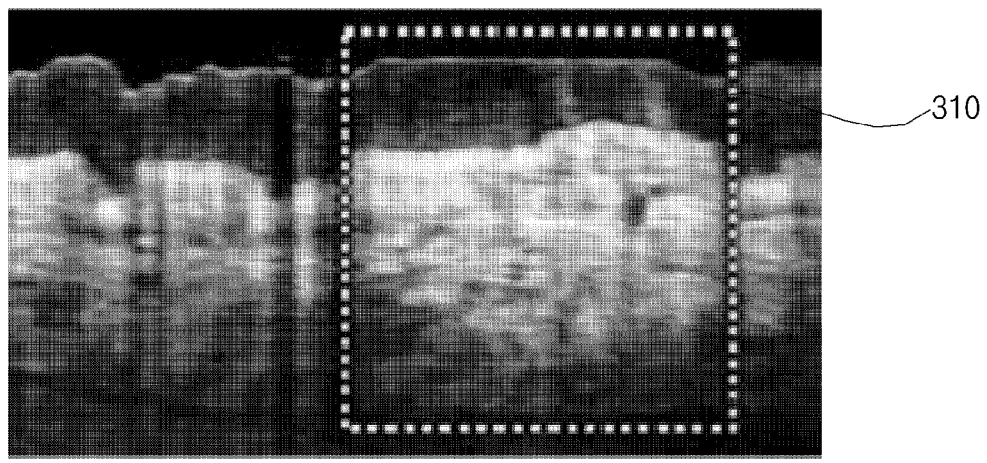
FIGS. 3A to 4D are diagrams referenced to explain operation of the OCT device shown in FIG. 1.

FIG. 3A is a diagram illustrating an example of a skin image 310 displayed on the display 180 of the OCT device 100.

The skin image 310 may include dermis at the bottom, epidermis above the dermis, and stratum corneum above the epidermis. If the dermis is dense, it may indicate that the skin is firm and elastic.

With such a skin image, it is possible to check the skin condition of a patient.

Figure 3B:
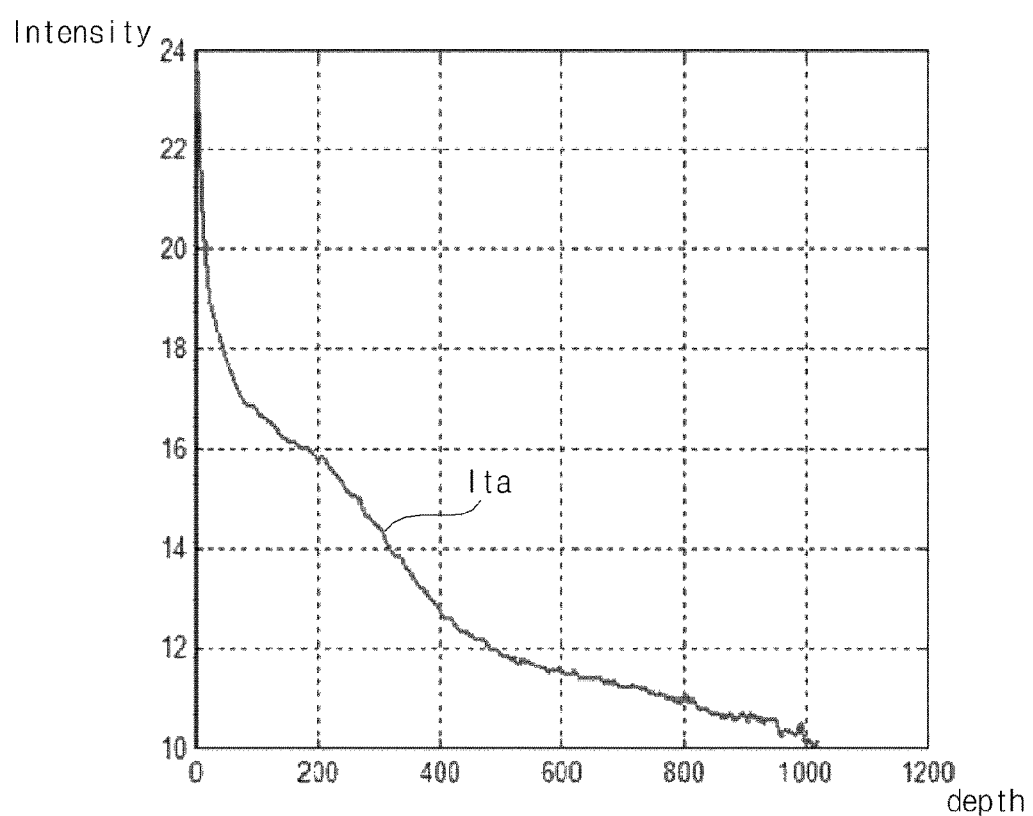

Meanwhile, the processor 170 and the like of the OCT device 100 analyzes the skin image 310 to calculate image intensity with respect to the depth (from the top to the bottom) of the skin image 310, as shown in FIG. 3B.

The image intensity may correspond to density of the skin. Accordingly, it is possible to calculate the density of the aforementioned dermis.

That is, FIG. 3B is an exemplary graph showing measured intensity information of a skin image 310.

The intensity information of the skin image 310 contains system properties of the OCT device 100, and thus, the properties need to be corrected.

Figure 3C:
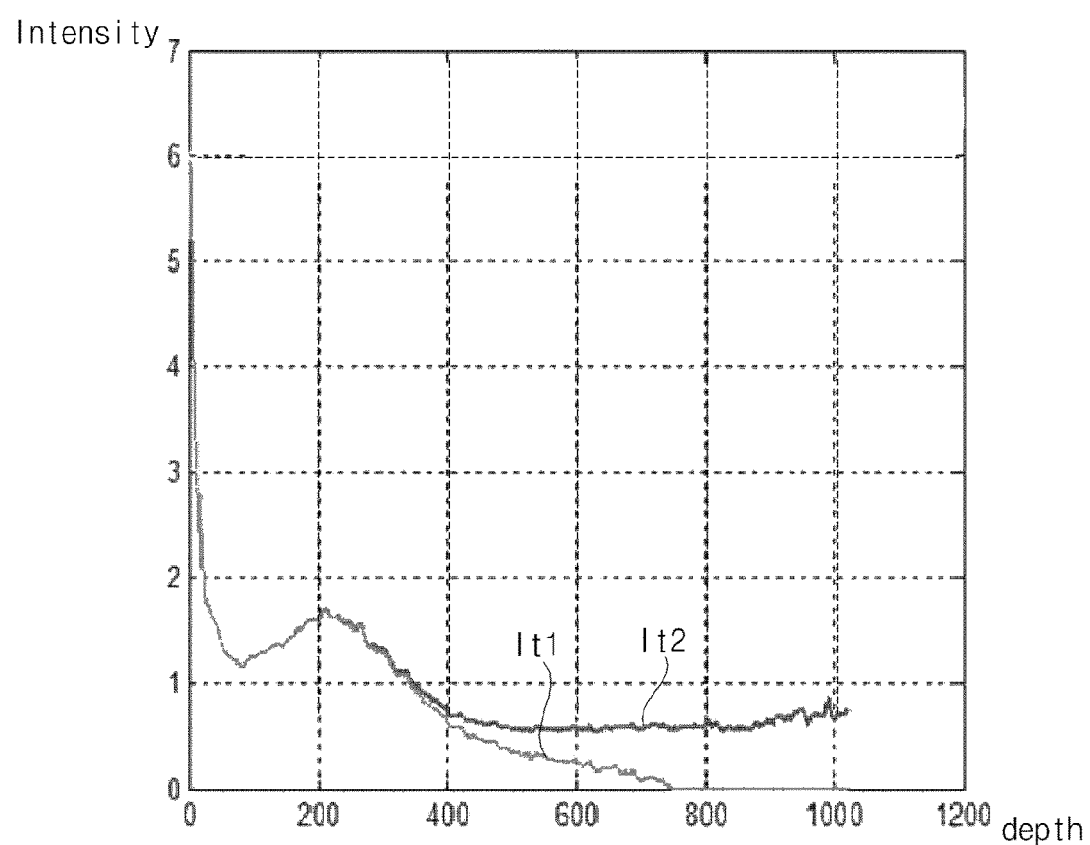
Figure 3D:
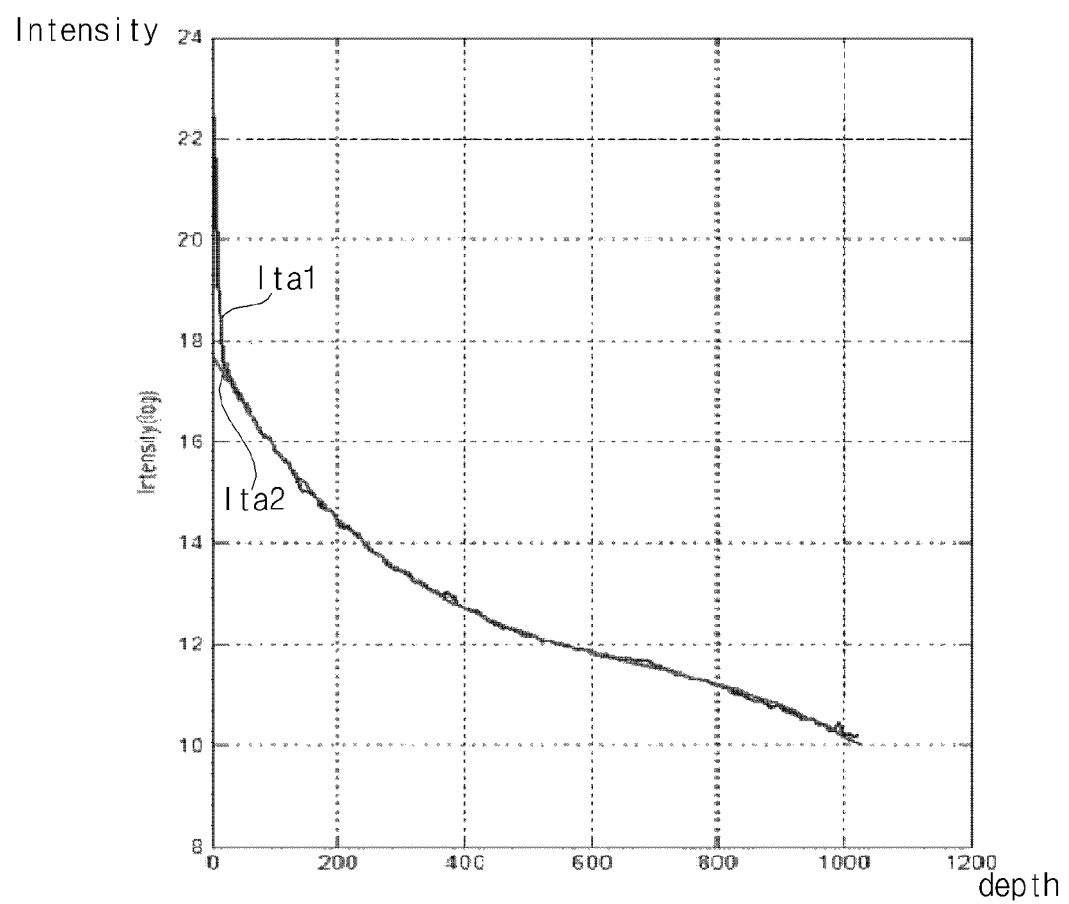

FIG. 3D is an exemplary graph showing intensity information of a skin image 310 for the purpose of calibration of the system properties of the OCT device 100.

The processor 170 may divide the graph of FIG. 3B by the graph of FIG. 3D, thereby enabled to calculate intensity information of the skin image 310 in which system properties have been corrected or calibrated.

Meanwhile, the first graph It1 in FIG. 3C is an exemplary graph showing measured intensity information of a skin image 310 in which system properties have been corrected and noise floor processing have been performed, and the second graph It2 is an exemplary graph showing measured intensity information of a skin image 310 in which system properties have been corrected but noise floor processing has not been performed.

As shown in the drawings, the greater the depth of the skin, the lesser the intensity of the skin image 310.

Figure 4A:
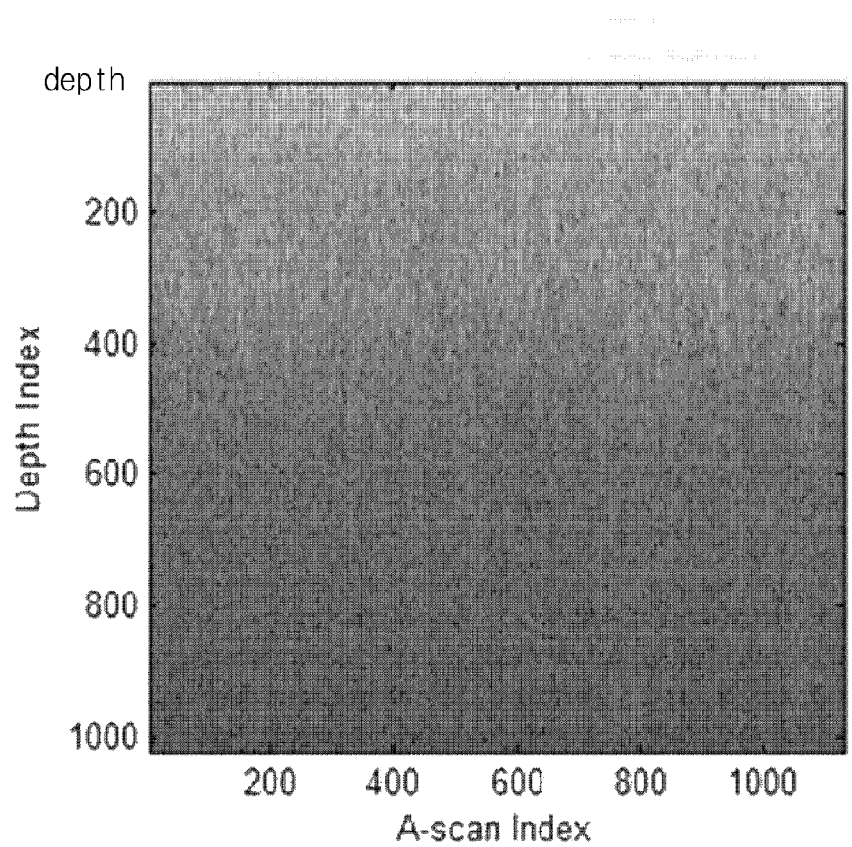
Figure 4B:
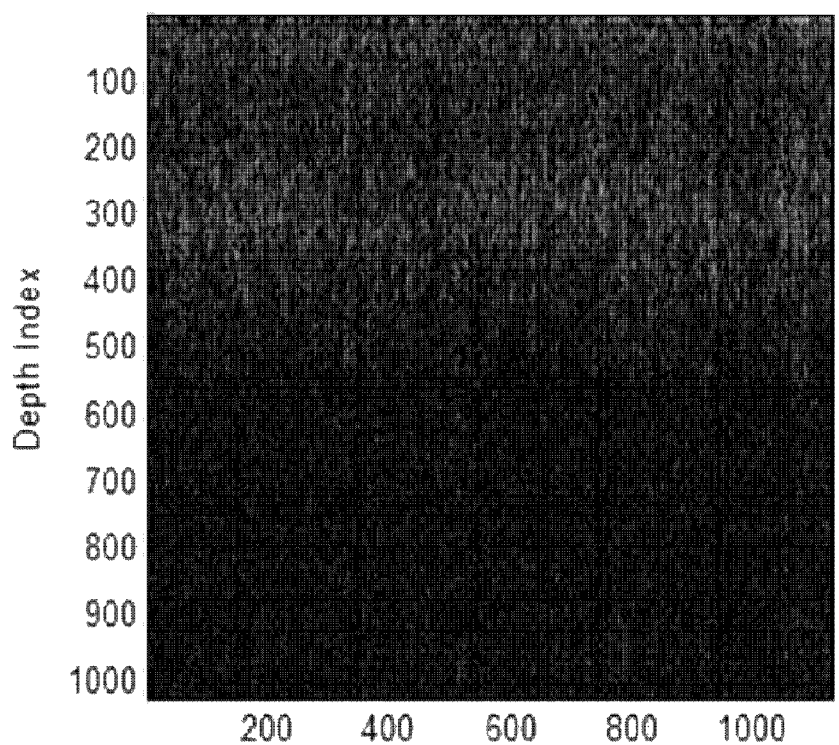

FIG. 4A shows an example of a skin image of a first patient, and FIG. 4B shows an example of a skin image of a second patient.

Figure 4C:
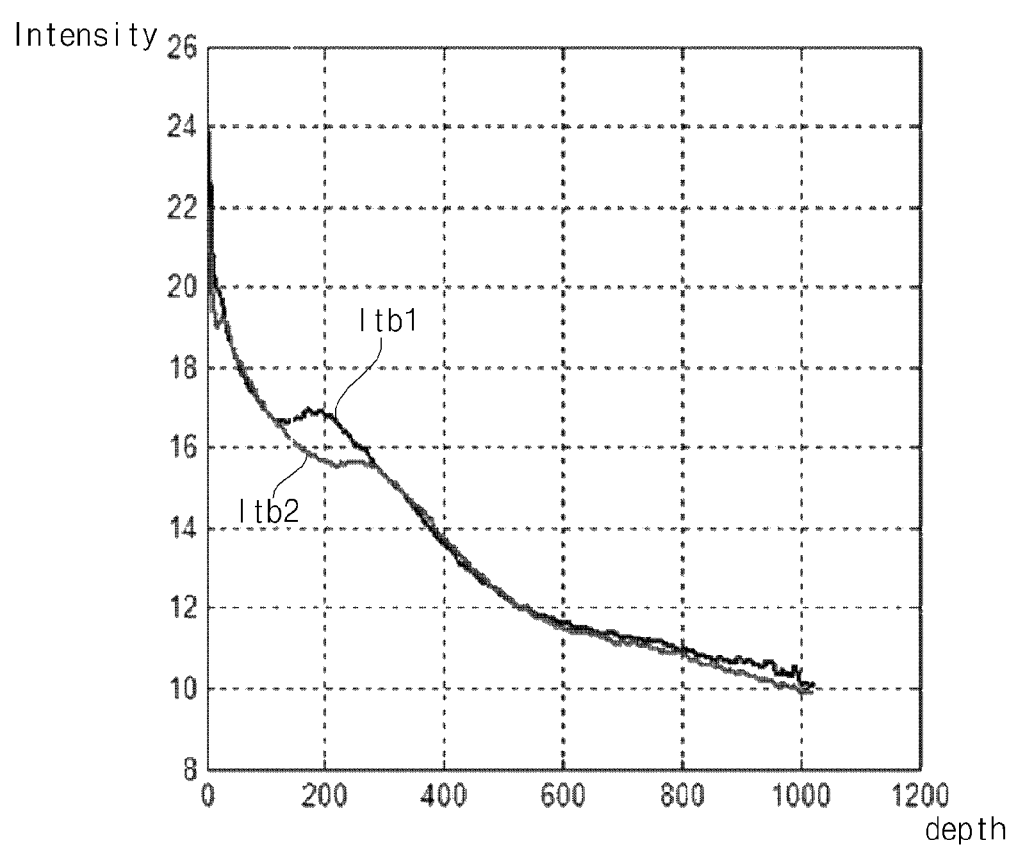

FIG. 4C is an exemplary graph showing intensity information of a not-calibrated image skin image 310 in which system properties have not been corrected.

In particular, there are shown a graph Itb1 showing intensity information of the skin image of the first patient, and a graph Itb2 showing intensity information of the skin image of the second patient.

Even though system properties are not corrected in the skin images, the intensity of the skin image of the first patient is greater than that of the skin image of the second patient, and thus, it is possible to assume that the skin of the first patient is denser than that of the second patient.

Figure 4D:
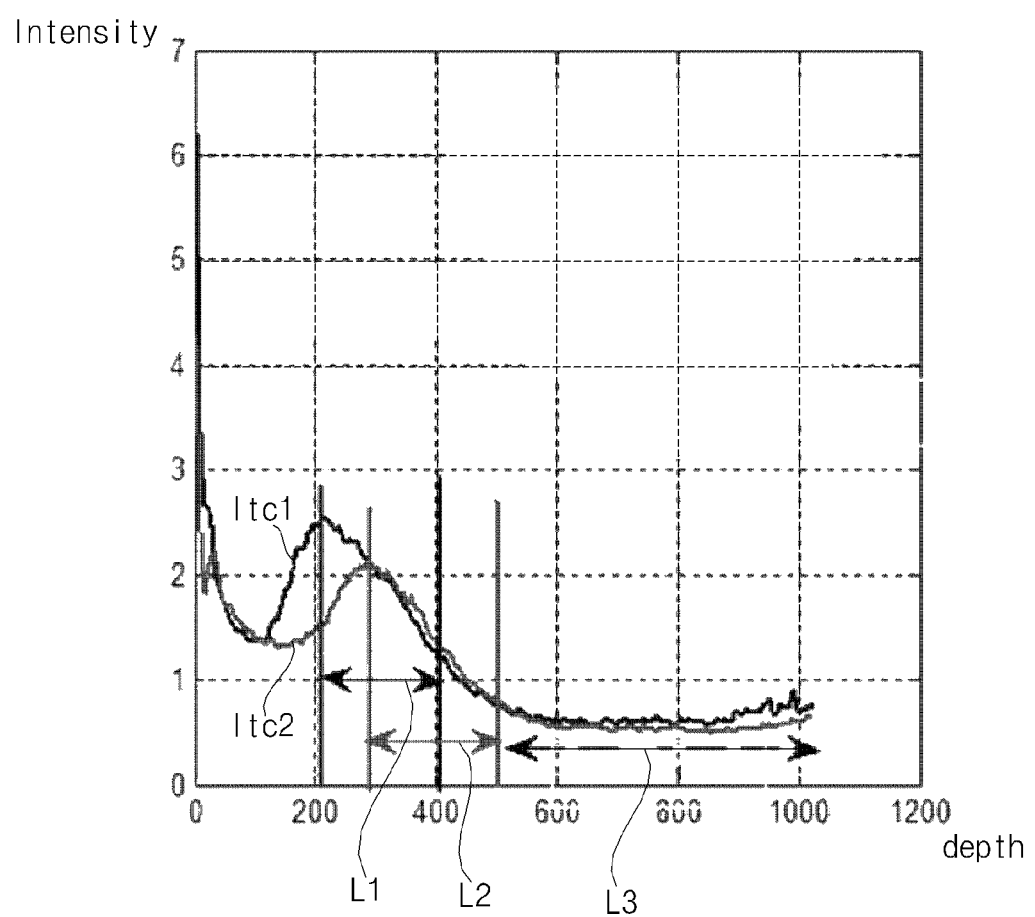

FIG. 4D is an exemplary graph showing intensity information of a calibrated skin image 310 indicating an image in which system properties have been corrected.

In particular, there are shown a graph Itc1 showing intensity information of the skin image of the first patient, and a graph Itc2 showing intensity information of the skin image of the second patient.

When the system properties are corrected in the skin images, the intensity of the skin image of the first patient is greater than that of the skin image of the second patient, and thus, it is possible to assume that the skin of the patient is denser than that of the second patient.

Figure 5:
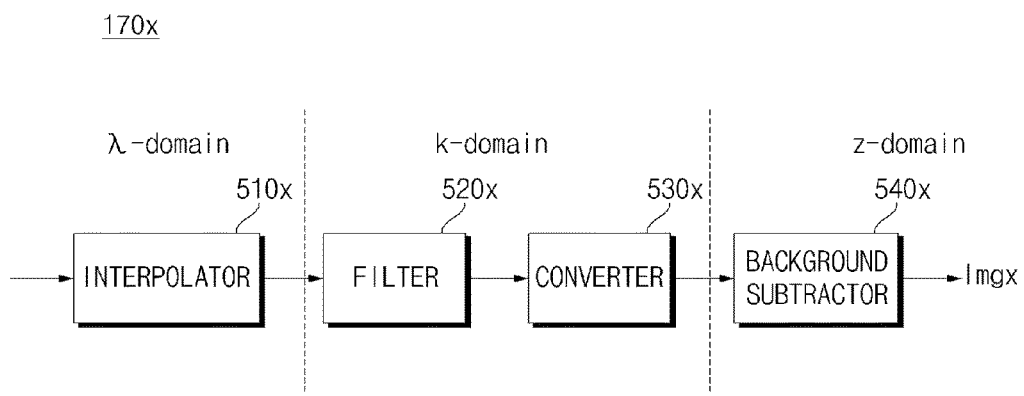
FIG. 5 is a diagram referenced to explain a processor.

FIG. 5 is a diagram referenced to explain a processor.

Referring to the drawing, a processor 170x shown in FIG. 5 may include an interpolator 510x, a filter 520x, a converter 530x, and a background subtractor 540x.

The interpolator 510x interpolates an image signal from an image sensor 160.

The filter 520x performs filtering on the interpolated image signal. The converter 530x converts the signal into frequency domain using Fourier Transform (FT). The background subtractor 540x may output a structural image (z-domain), from which a background has been removed, using reference subtraction.

Meanwhile, the image sensor 160 includes a plurality of pixels, and thus, if the pixels have non-uniform properties, a Photo-Response Non-Uniformity (PRNU) noise signal may occur due to the image sensor. In addition, due to the noise, an unclear skin image may be acquired.

The present invention proposes a method of reducing a PRNU noise, caused by an image sensor, to display a skin image with improved quality. Detailed descriptions thereof are provided with reference to FIG. 6.

Figure 6:
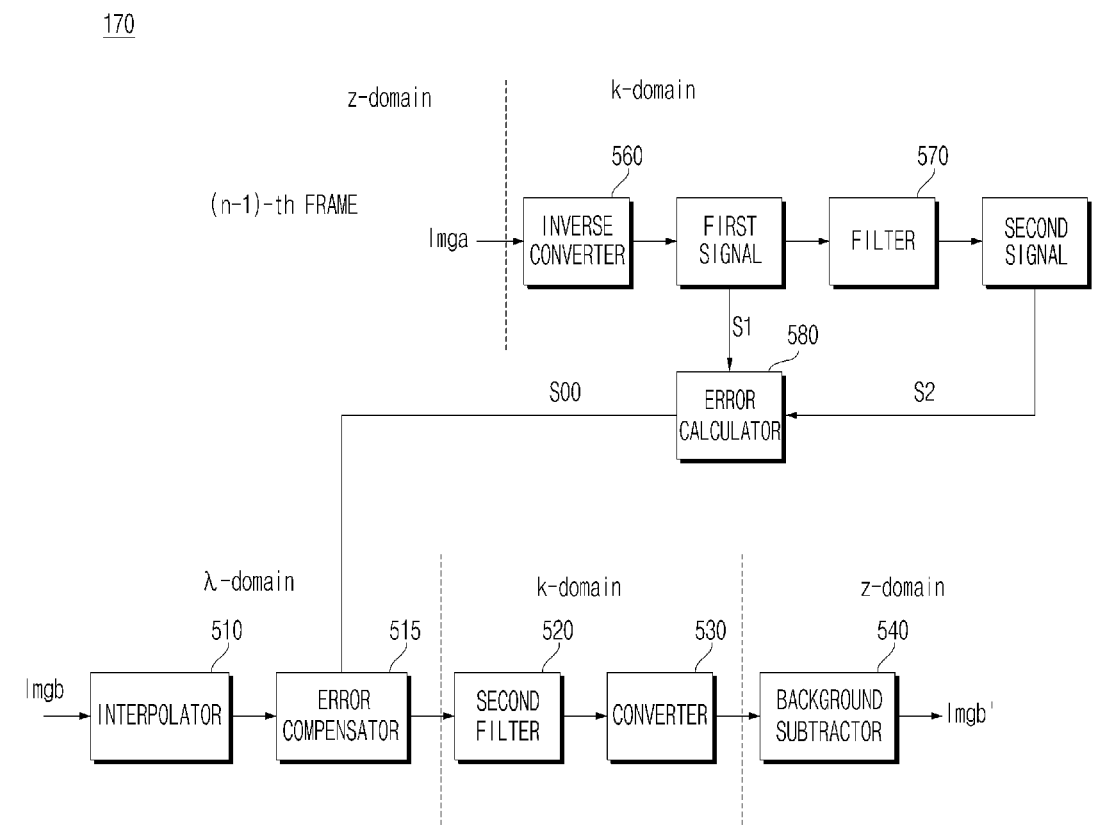
FIG. 6 is an internal block diagram illustrating an example of the OCT device shown in FIG. 2.

FIG. 6 is a block diagram illustrating an example of a processor of the OCT device shown in FIG. 2, and FIGS. 7A to 8B are diagrams referenced to explain operation of the processor shown in FIG. 6.

For starters, referring to FIG. 6, a processor 170 of the OCT device 100 according to an embodiment of the present invention may include an interpolator 510, an error compensator 515, a second filter 520, a converter 530, a background subtractor 540, an inverse-converter 560, a filter 570, and an error calculator 580.

The processor 170 may output a second signal by filtering a first signal being based on an image signal from the image signal 160, calculate an error by using the first and second signal, and outputs an error-compensated image by compensating for the calculated error.

In particular, during a first frame interval, the processor 170 may output a second signal by filtering a first signal being based on an image signal from the image sensor 160, and calculate an error using the first signal and the second signal. Then, during a second frame interval, the processor 170 may output an error-compensated image by compensating for the calculated error. In this manner, it is possible to perform error compensation in real time and therefore display a skin image with improved quality.

Meanwhile, the processor 170 may calculate the error based on a ratio between the first signal and the second signal, compensate the image signal from the image sensor 160 by using an inverse of the calculated error, and output the error compensated image.

Meanwhile, the processor 170 may perform error compensation on each horizontal or vertical line of the image signal from the image sensor 160.

Meanwhile, if image signals are received from the image sensor 160, the processor 170 may continuously perform error compensation. In this manner, it is possible to perform error compensation in real time and therefore display a skin image with improved quality.

Meanwhile, the processor 170 may include the filter 570 for outputting a second signal by filtering a first signal, and the filter 570 may output the second signal based on a moving average of the first signal.

Meanwhile, the processor 170 may include: the interpolator 510 for interpolating an image signal from the image sensor; the error compensator 515 for compensating the interpolated image signal by using a calculated error; the converter 530 for converting the error-compensated image signal into frequency domain; and the background subtractor 540 for removing a background from an image signal from the converter 530 and outputs an error-compensated image from which the background has been removed.

Meanwhile, the processor 170 may further include: the inverse converter 560 for converting an image signal from the background subtractor 540 into time domain; the filter 570 for outputting a second signal by filtering a first signal from the inverse-converter 560; and the error calculator 580 for calculating an error using the first signal and the second signal.

Meanwhile, the processor 170 may further include the second filter 520 which is disposed (e.g., coupled) between the error compensator 515 and the converter 530 and to filter an error, caused by a mirror 135, from the error-compensated image signal.

Meanwhile, during a first frame interval, the processor 170 may output a second signal by filtering a first signal being based on an image signal from the image sensor, and calculate an error using the first signal and the second signal by means of the inverse converter 560, the filter 570, and the error calculator 580. Then, during a second frame interval, the processor 170 may output an error-compensated image by compensating for the calculated error by means of the error calculator 580, the converter 530, and the background subtractor 540.

In more details of the above-described operation of the processor 170, the (n−1)-th frame image Imga, on which signal processing is performed by the image sensor 160 or the processor 170, is input to the inverse converter 560.

In particular, the inverse converter 560 may receive the (n−1)-th frame image Imga from the background subtractor 540.

The inverse converter 560 converts an image signal from frequency domain, into time domain. That is, the inverse converter 560 outputs a first signal S1 in the time domain by inverting an image signal using Inverse Fourier Transform (IFT).

Then, the filter 570 outputs a second signal S2 by filtering a first signal S1.

Meanwhile, the filter 570 may output the second signal S2 based on a moving average of the first signal S1.

Figure 7A:
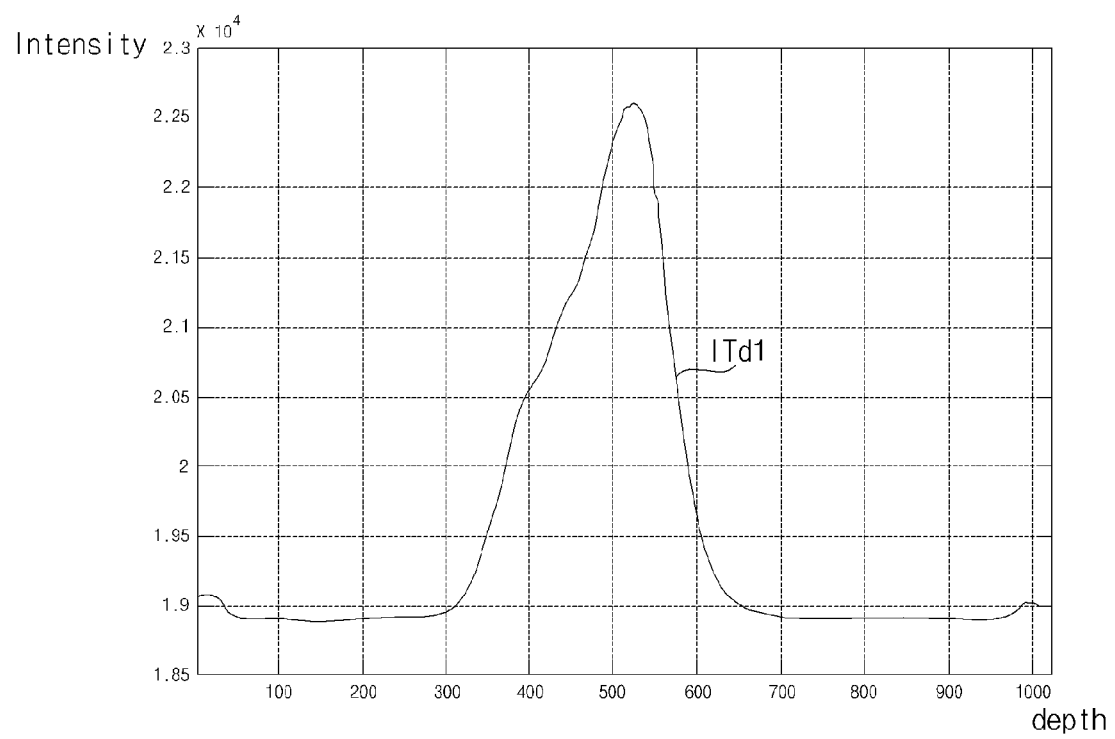
FIGS. 7A to 8B are diagrams referenced to explain operation of the processor shown in FIG. 6.
Figure 7B:
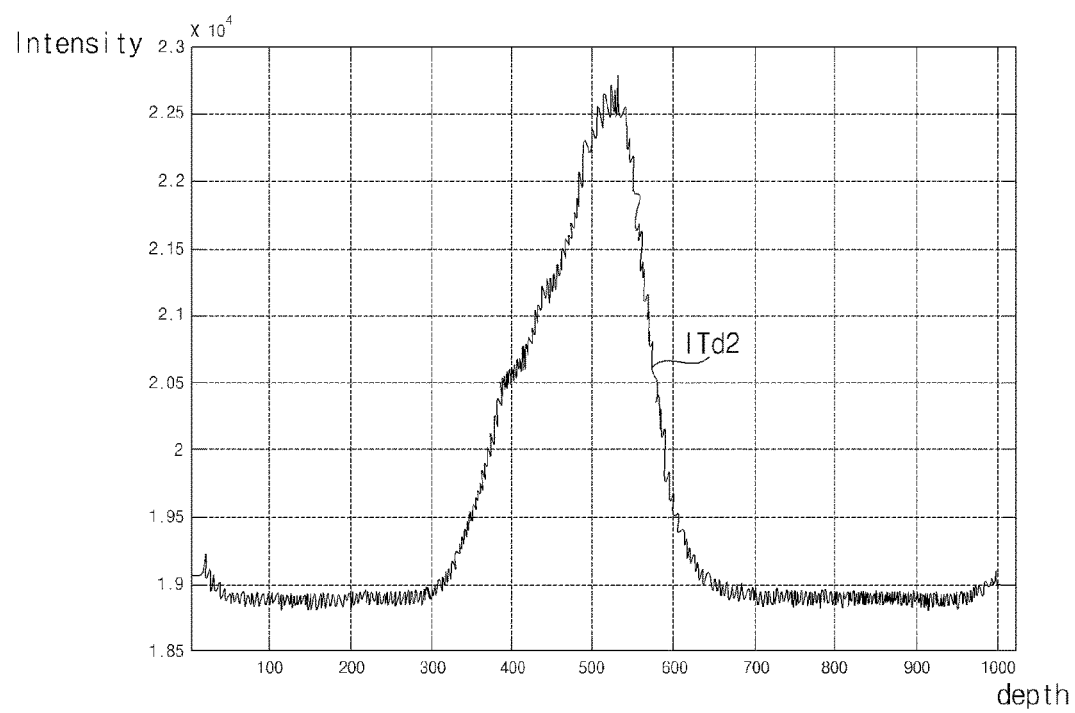

FIG. 7A shows a graph Itd1 indicating measured intensity corresponding to the first signal S1 with respect to depth of skin, and FIG. 7B shows a graph Itd2 indicating measured intensity corresponding to the second signal S2 with respect to depth of skin.

Next, the error calculator 580 may calculate an error by using the first signal S1 and the second signal S2.

In particular, the error calculator 580 may calculate the error based on a ratio between the first signal S1 and the second signal S2.

More specifically, the error calculator 580 may calculate an error Soo by dividing the first signal S1 by the second signal S2.

Figure 7C:
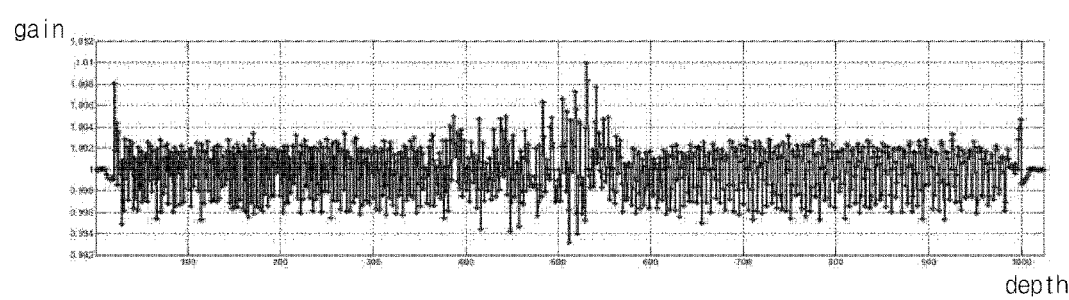

FIG. 7C shows an example of an error which is calculated by dividing the first signal S1 by the second signal S2.

In particular, the error calculator 580 may calculate a gain of an error with respect to depth of skin, as shown in FIG. 7C, by dividing a gain of the first signal S1 by a gain of the second signal S2. Meanwhile, the calculated error Soo is used for compensating for an error in the n-th frame.

The interpolator 510 receives an image signal of the n-th frame from the image sensor 160, and interpolates the image signal from the image sensor 160.

Next, the error compensator 515 performs error compensation on the image signal of the n-th frame, which is received from the interpolator 510, by using the error Soo that is calculated with respect to the (n−1)-th frame.

For example, the error compensator 515 may compensate for an error of an image signal from the image sensor 160 by using 1/Soo which is an inverse of the error Soo, and may output an error compensated image.

The error compensator 515 may perform error compensation on each horizontal or vertical line of the image signal from the image sensor 160.

If image signals are received from the image sensor 160, the error compensator 515 may continuously perform error compensation.

During a first frame interval, the error calculator 580 may output a second signal by filtering a first signal being based on an image signal from the image sensor 160, and calculate an error by using the first signal and the second signal. During a second frame interval, the error compensator 515 may output an error-compensated image by compensating for the calculated error.

Next, the second filter 520 performs filtering on an error-compensated signal in the k-domain.

Next, the converter 530 may convert the error-compensated image signal into a frequency domain using Fourier Transform (FT).

The background subtractor 540 may remove a background from the image signal, and output an error-compensated image Imgb' from which the background has been removed.

The display may display the error-compensated image Imgb'. Accordingly, noise caused by the image sensor may be reduced, and therefore, a skin image with improved quality may be displayed. In particular, it is possible to display an image in which an error has been compensated with respect to depth of skin.

Meanwhile, the background subtractor 540 may transfer the error-compensated image Imgb' to the inverse converter 560 in order to perform error calculation on the (n+1)-th frame.

Figure 7D:
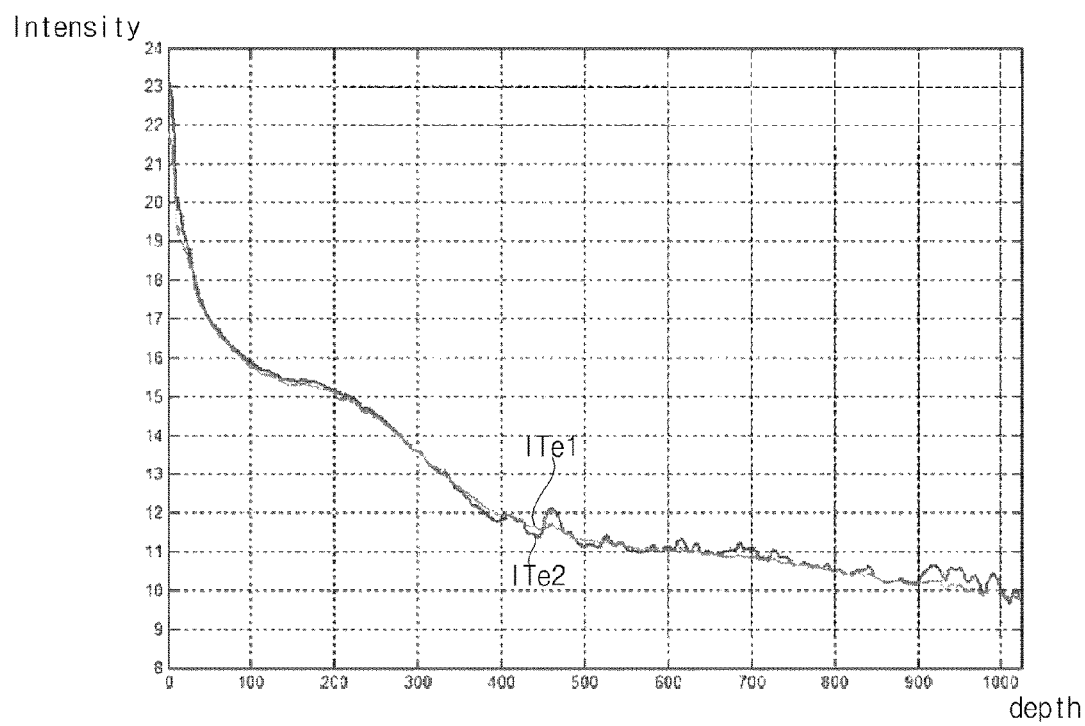

FIG. 7D shows a graph Ite1 indicating intensity of which PRNU noise has been compensated with respect to depth of skin, a graph Ite2 showing intensity of which PRNU noise has not been compensated with respect to depth of skin.

In the graph Ite2, that the greater the depth of the skin, the greater the PRNU noise. However, the graph Ite1 has a smooth line even at a great depth of the skin because noise has been removed.

Accordingly, it is possible to obtain a clear skin image with noise removed, no matter how great the depth of the skin may be.

Figure 8A:
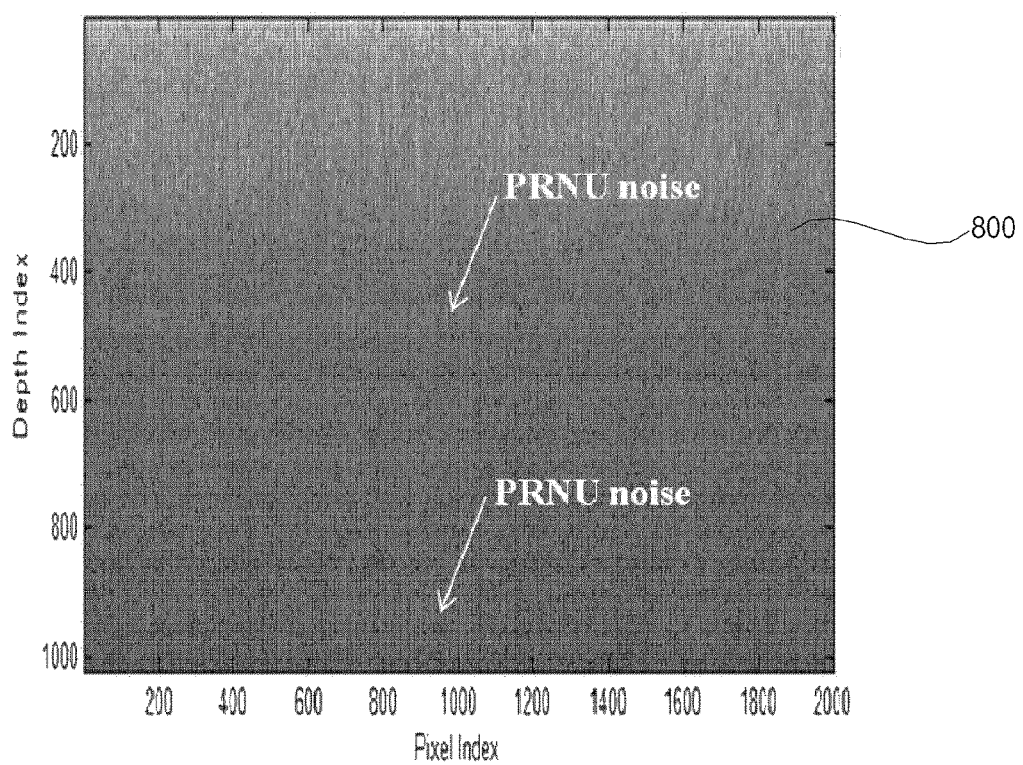
Figure 8B:
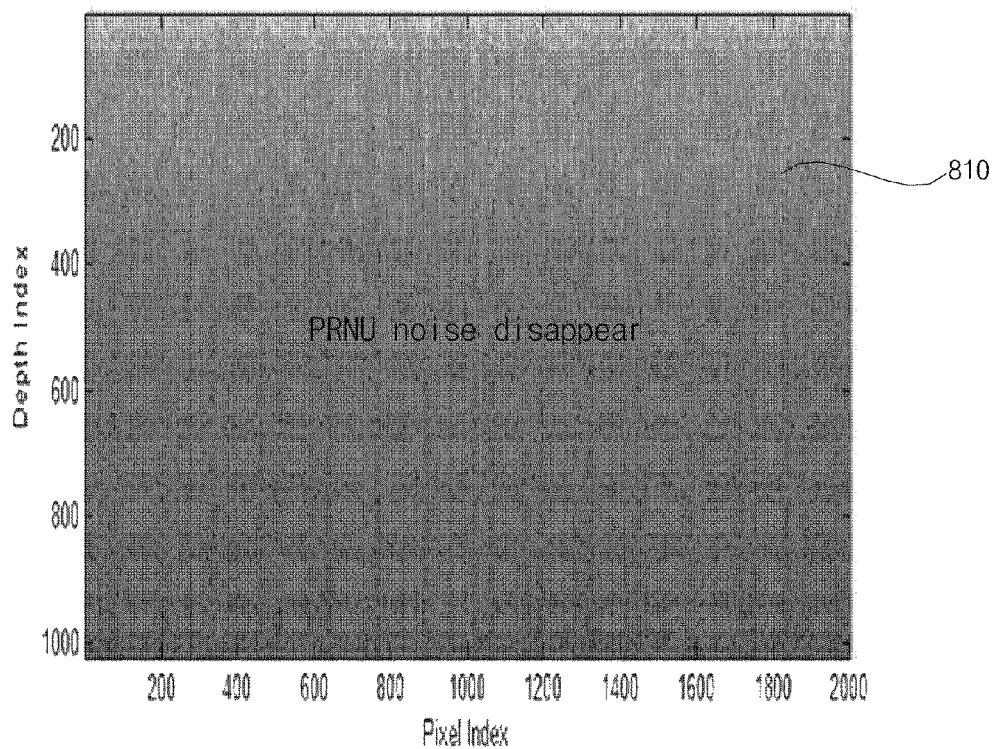

FIG. 8A shows an example of a skin image 800 of which PRNU noise has not been compensated, and FIG. 8B shows an example of a skin image 810 of which PRNU noise has been compensated.

As shown in FIG. 8B, according to the OCT device 100, noise caused by an image sensor may be reduced, and therefore, a skin image with improved quality may be displayed. In particular, it is possible to display an image in which an error has been compensated with respect to depth of skin.

An OCT device according to an embodiment of the present invention should not be limited to the configurations and methods shown in the above-described embodiments, and the embodiments may be modified by combining all or some of the embodiments.

As is apparent from the foregoing description, an OCT device according to an embodiment of the present invention includes: a light source; a mirror to reflect a light from the light source; a light receiver to output a light from the light source to the skin and receive a light reflected from the skin; and a detector to receive an interference signal between the light reflected from the mirror and a light received by the light receiver; an image sensor to convert the interference signal, detected by the detector, into an image signal; a processor to output a second signal by filtering a first signal being based on the image signal from the image sensor, calculate an error by using the first signal and the second signal, and output an error-compensated image by compensating for the calculated error; and a display to display the error-compensated image. In this configuration, the OCT device may reduce noise caused by the image sensor, thereby enabled to display a skin image with improved quality. In particular, it is possible to display an image in which an error has been compensated with respect to depth of skin.

In particular, during a first frame interval, the processor outputs a second signal by filtering a first signal being based on an image signal from the image sensor, and calculates an error by using the first signal and the second signal. Then, during a second frame interval, the processor outputs an error-compensated image by compensating for the calculated error. In this manner, it is possible to perform error compensation in real time and therefore display a skin image with improved quality.

Meanwhile, when image signals are received from the image sensor, the processor continuously performs error compensation. In this manner, it is possible to perform error compensation in real time and therefore display a skin image with improved quality.

Meanwhile, an OCT device according to another embodiment of the present invention includes: a probe to output a light to the skin and receive a light reflected from the skin; a spectrometer to detect an interference signal between a light reflected from a mirror and a light received by the probe; an image sensor to convert the interference signal, received from the spectrometer, into an image signal; a processor to calculate an error caused by a difference in pixels of the image sensor, and output an error-calculated image by compensating for the calculated error; and a display to display an error-compensated image. In this configuration, the OCT device may reduce noise caused by the image sensor, thereby enabled to display a skin image with improved quality.

While the apparatus and methods of the subject invention have been shown and described with reference to preferred embodiments, those skilled in the art will readily appreciate that various changes and/or modifications may be made thereto without departing from the spirit and scope of the subject invention as defined by the appended claims.

What is claimed is:

1. An Optical Coherence Tomography (OCT) device comprising:
   a light source;
   a mirror to reflect a light from the light source;
   a light receiver to output the light from the light source to skin, and receive a light reflected from the skin;
   a detector to detect an interference signal between the light reflected from the mirror and the light received by the light receiver;
   an image sensor to convert the detected interference signal into an image signal;
   a processor electrically connected to the image sensor, and configured to filter a first signal based on the image signal in order to output a second signal, calculate an error by using the first signal and the second signal, and output an error-compensated image by compensating for the calculated error; and
   a display to display the error-compensated image, wherein the processor calculates the error based on a ratio between the first signal and the second signal, and compensates for the calculated error by using an inverse of the calculated error.

2. The OCT device according to claim 1, wherein:
during a first frame interval, the processor outputs the second signal and calculates the error; and
during a second frame interval, the processor outputs the error-compensated image.

3. The OCT device according to claim 1, wherein the processor performs error compensation on each horizontal line or each vertical line of the image signal.

4. The OCT device according to claim 1, wherein, when image signals are received from the image sensor, the processor continuously performs the error compensation.

5. The OCT device according to claim 1, wherein the processor comprises a filter to output the second signal by filtering the first signal, and
wherein the filter outputs the second signal based on a moving average of the first signal.

6. The OCT device according to claim 1, wherein the processor comprises:
an interpolator to interpolate the image signal;
an error compensator to compensate for one or more errors in the interpolated image signal by using the calculated error, and output an error-compensated image signal;
a converter to convert the error-compensated image signal into a frequency domain; and
a background subtractor to remove a background from the converted error-compensated image signal, and output the error-compensated image.

7. The OCT device according to claim 6, wherein the processor further comprises:
an inverse converter to output the first signal by converting the background-removed image signal into a time domain;
a filter to output the second signal by filtering the first signal; and
an error calculator to calculate the error by using the first signal and the second signal.

8. The OCT device according to claim 7,
wherein, during a first frame interval, the processor outputs the second signal via the inverse converter, the filter and the error calculator, and calculates the error, and
wherein, during a second frame interval, the processor outputs the error-compensated image via the error compensator, the converter and the background subtractor.

9. The OCT device according to claim 6, wherein the processor further comprises a filter, coupled between the error compensator and the converter, to filter an error, caused by the mirror, from the error-compensated image signal.

10. The OCT device of claim 1, further comprising a probe that comprises the mirror and the light receiver.

11. The OCT device according to claim 1, wherein the detector comprises a spectrometer to decompose the interference signal into different wavelengths, and
wherein the image sensor outputs the image signal by detecting the decomposed interference signal at each pixel.

12. The OCT device according to claim 1, wherein the display displays the error-compensated image which corresponds to a depth of the skin.

13. An Optical Coherence Tomography (OCT) device comprising:
a probe to output a light to skin and receive a light reflected from the skin;
a spectrometer to detect an interference signal between a light reflected from a mirror and the light received by the probe;
an image sensor to convert the detected interference signal into an image signal;
a processor electrically connected to the image sensor, and configured to calculate an error in the image signal, the error caused by a difference in pixels of the image sensor, and output an error-compensated image by compensating for the calculated error; and
a display to display the error-compensated image,
wherein the processor calculates the error by using a first signal and a second signal,
wherein the first signal is based on the image signal, and the second signal is calculated based on a moving average of the first signal, and
wherein the processor calculates the error based on a ratio between the first signal and the second signal, and compensates for the calculated error using an inverse of the calculated error.

14. The OCT device according to claim 13,
wherein, during a first frame interval, the processor filters a first signal based on the image signal in order to output a second signal, and calculates the error by using the first signal and the second signal, and
wherein, during a second frame interval, the processor outputs the error-compensated image.

15. The OCT device according to claim 13, wherein the processor comprises:
an interpolator to interpolate the image signal;
an error compensator to compensate for one or more errors in the interpolated image signal by using the calculated error, and output an error-compensated image signal;
a converter to convert the error-compensated image signal into a frequency domain; and
a background subtractor to remove a background from the converted error-compensated image signal, in order to output the error-compensated image.

16. The OCT device according to claim 15, wherein the processor further comprises:
an inverse converter to output a first signal by converting the background-removed image signal into a time domain;
a filter to output a second signal by filtering the first signal; and
an error calculator to calculate the error by using the first signal and the second signal.

17. The OCT device according to claim 16,
wherein, during a first frame interval, the processor outputs the second signal via the inverse converter, the filter and the error calculator, and calculates the error, and
wherein, during a second frame interval, the processor outputs the error-compensated image via the error compensator, the converter and the background subtractor.

* * * * *